Jan. 30, 1940. C. SALBACH Plant Pat. 357
GLADIOLUS
Filed March 22, 1939
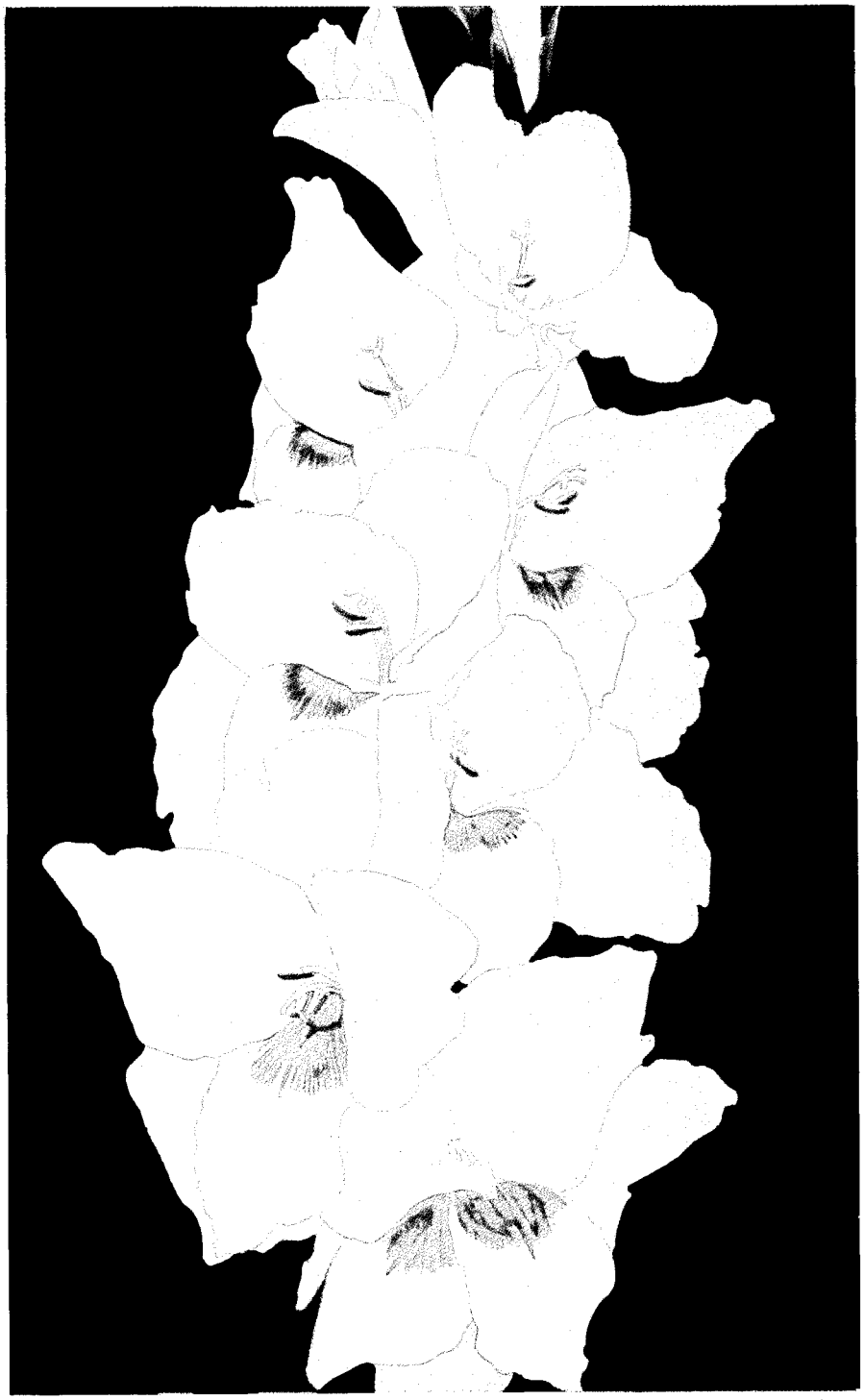
Inventor—Carl Salbach
By Orville M. Kile—Plant Patent Agent Patented Jan. 30, 1940

Plant Pat. 357

UNITED STATES PATENT OFFICE

357

GLADIOLUS

Carl Salbach, Contra Costa County, Calif., assignor to Ella S. Salbach, Contra Costa County, Calif.

Application March 22, 1939, Serial No. 263,528

1 Claim. (Cl. 47—60)

My present invention relates to improvements in flowering gladioli of the type notable for quality and size of bloom. The object of this invention is to provide a superior gladiolus of the color commonly called apricot, having at the same time large flowers which are well placed and well formed, and are consistent in growing in this manner.

My new gladiolus variety originated as a seedling produced from cross pollination work carried on by myself and is a cross between Grand Opera (Plant Patent No. 280) as the pollen parent and Picardy as the seed parent. The variety has been reproduced asexually through several generations and its qualities have proved to be permanently fixed.

The illustration accompanying this specification shows a portion of a spike of this variety in approximately its true color but reduced in size.

Color plate references are to Ridgway's Color Standards and Nomenclature.

Following is a more complete description of the plant and flower of this new variety.

*The plant*

Growth:

Very vigorous, the tips of the spike usually standing four feet above the ground in my gardens. Very consistent in producing fine spikes upon which the flowers are placed in symmetrical position, all facing in one direction.

Blooming:

Usually each spike opens up six to eight of its large flowers at once, and has sixteen to eighteen flowers in all.

Foliage:

Usually seven leaves. Broad. Straight. Oriental Green (Plate XVIII).

Stems:

Stiff, strong and straight.

Spike:

Spike or flower-head exceptionally long, being 24 inches in length.

Corm:

Medium in size. Yellow when peeled.

*The flower*

The blossom:

Consists of six petals.

*Size.*—Generally six to seven inches across, although some run to seven and one-half inches.

*Form.*—Very nearly square in form, although they could also be compared to a very blunt five-pointed star (formed by six petals).

*Petals.*—Shape—blunt. Aspect—faintly fluted, edges slightly ruffled. Substance—heavy, making the variety very valuable for shipping and long keeping. Color—the color in Ridgway's Color Standards which most nearly approaches the color of this variety is Safrano Pink (Plate II), with the blotch, which is deep in the throat, being best described as Ocher Red (Plate XXVII) faintly fringed with Coral Red (Plate XIII). The coloring of this variety has a very soft appearance.

*Stamens.*—Filaments Safrano Pink. Most of the anthers of the same color on top but Dark Dull Violet Blue (Plate XXIV) underneath where they are covered with pollen. Some anthers do not carry pollen and these are cream color (Plate XVI).

*Pistils.*—Medium size. Cream color (Plate XVI).

*Comparison*

Other known varieties of somewhat similar coloring have either smaller flowers or less vivid coloring. The former is true of such varieties as Wasaga, while the varieties Opal Queen and Paradise, although approaching the size of my new variety are, in the opinion of observers, of greatly inferior coloring, Opal Queen being somewhat honey-colored and Paradise carrying more yellow and less pink in its coloring.

The most notable characteristics which in combination readily distinguish my new gladiolus from other known "apricot" gladioli, particularly the varieties Wasaga, Opal Queen, and Paradise, are:

1. The soft coloring of the flowers.
2. The unusual color pattern of the flowers.
3. The large size of the flowers.
4. The heavy substance with resultant fine keeping quality.
5. The vigor and height of the plant, and the length of the flower-head.
6. The consistency of the ideally symmetrical growth, as described.

Having thus disclosed my invention, I claim:

The new variety of gladiolus herein described and illustrated, characterized particularly by its vigorous, symmetrical and consistent growth; length of flower-head; and flowers of very large size, good substance, excellent keeping quality, and soft coloring of Safrano Pink with darker blotches, as described and shown.

CARL SALBACH.